United States Patent [19]

Müller et al.

[11] Patent Number: 5,248,767
[45] Date of Patent: Sep. 28, 1993

[54] PROCESS FOR THE PREPARATION OF A PASTEURIZED IMMUNOGLOBULIN PREPARATION USING ETHANOL

[75] Inventors: Hans Müller, Dautphetal; Helmut Geiger, Marburg, both of Fed. Rep. of Germany

[73] Assignee: Behringwerke Aktiengesellschaft, Marburg, Fed. Rep. of Germany

[21] Appl. No.: 989,953

[22] Filed: Dec. 10, 1992

Related U.S. Application Data

[63] Continuation of Ser. No. 839,079, Feb. 24, 1992, abandoned, which is a continuation of Ser. No. 555,674, Jul. 19, 1990, abandoned, which is a continuation of Ser. No. 391,397, Aug. 9, 1989, abandoned, which is a continuation of Ser. No. 59,846, Jun. 9, 1987, abandoned.

[30] Foreign Application Priority Data

Jun. 11, 1986 [DE] Fed. Rep. of Germany ....... 3619565

[51] Int. Cl.$^5$ .................. C07K 15/14; A61K 39/395
[52] U.S. Cl. .............................. 530/390.1; 530/387.1; 530/390.5; 424/85.8
[58] Field of Search ............... 530/387.1, 390.1, 390.5; 424/85.8

[56] References Cited

U.S. PATENT DOCUMENTS

| | | | |
|---|---|---|---|
| 3,100,737 | 8/1963 | Auerswald et al. | 530/387 X |
| 4,164,495 | 8/1979 | Hansen | 530/387 |
| 4,579,735 | 4/1986 | Heimburger et al. | 424/101 |
| 4,640,834 | 2/1987 | Eibl et al. | 424/101 X |
| 4,687,664 | 8/1987 | Philapitsch et al. | 424/101 X |
| 4,721,777 | 1/1988 | Uemura et al. | 530/387 X |
| 4,762,714 | 8/1988 | Mitra et al. | 530/387 |

FOREIGN PATENT DOCUMENTS

| | | |
|---|---|---|
| 058993A2 | 9/1982 | European Pat. Off. . |
| 0139975A1 | 8/1984 | European Pat. Off. . |
| 0177836A3 | 10/1986 | European Pat. Off. . |
| 0196761A3 | 10/1986 | European Pat. Off. . |

OTHER PUBLICATIONS

Abstract of Japanese 042917, Sep. 1983, Green Cross.
Noller, Chemistry of Organic Compounds (1957), pp. 412-413.
The Condensed Chemical Dictionary, Eighth Edition, Revised by Gessner G. Hawley, Van Nostrand Reinhold Company (1971) p. 833.

*Primary Examiner*—Howard E. Schain
*Attorney, Agent, or Firm*—Finnegan, Henderson, Farabow, Garrett & Dunner

[57] ABSTRACT

A process for the production of a pasteurized immunoglobulin preparation is described, which comprises heating a solution of an immunoglobulin in the presence of a carboxylic acid or one of its salts and/or of a saccharide until viable pathogens, which may remain undetected in conventional tests, in particular hepatitis viruses or HTLV III ("Aids") viruses, are inactivated i.e. are rendered incapable of reproduction and/or of being intracellularly or otherwise reproduced.

A preparation of this type can be used for therapy or prophylaxis or as component of a diagnostic kit.

11 Claims, No Drawings

PROCESS FOR THE PREPARATION OF A PASTEURIZED IMMUNOGLOBULIN PREPARATION USING ETHANOL

This application is a continuation, of application Ser. No. 07/839,079, filed Feb. 24, 1992, now abandoned, which is a continuation of 07/555,674, filed Jul. 19, 1990, abandoned, which is a continuation of application Ser. No. 07/391,397, filed Aug. 9, 1989, abandoned, which is a continuation of application Ser. No. 07/059,846, filed on Jun. 9, 1987, abandoned.

The invention relates to a process for the production of an immunoglobulin preparation, in which, for the purpose of inactivation of pathogens, a solution of an immunoglobulin is heated in the presence of stabilizers and is, if necessary, subsequently purified.

A process is needed which permits inactivation of pathogens, such as viruses, by pasteurization of immunoglobulin preparations; thereby the full activity of the immunoglobulin must be retained. In general, when immunoglobulins are prepared by conventional processes there is a reduction in the potential risk of infection to such an extent that the content of viruses or viral antigens is often merely reduced to below the detection limit of the test system used. However, the detection limit is either usually inadequate to unambiguously rule out a risk of infection; or further, there are not test systems appropriate for detecting certain contamination viruses. Hence a heat treatment is expedient. It is claimed that the inactivation renders the infectious agent incapable of reproduction and/or of being intracellularly or otherwise reproduced.

To avoid their denaturation it is necessary to stabilize the immunoglobulins during their prolonged exposure to heat. To inactivate viruses it is indispensable to heat at the highest permissable temperature for a prolonged period.

A process is described in EP-A-0 124 506, in which ammonium sulfate is added to an immunglobulin solution, and the suspension is heated at 60° C. for 10 hours. However, when an immunoglobulin solution is treated as described in Example 16 of that patent application, the formation of polymeric immunoglobulin occurs. A maximum limit of 10% of polymeric immunoglobulin is permitted in the European Pharmacopoea in an immunoglobulin solution for intramuscular administration.

In EP-A-0 144 714 it is described that a Cohn fraction II+III (J. Am. Chem. Soc. (1946) 68, 459) can be pasteurized only under mild conditions, preferably at 52° C. for about 30 minutes; even when there has been previous removal of the euglobulins and dialysis of the solution to remove ethanol, aggregates are nevertheless produced. It is doubtful whether absolute virus inactivation is reliable under these conditions.

In The Lancet, of Nov. 19, 1983, pages 1198-99, there is a description of a process in which human immunoglobulin was heated to 60° C. for 10 h in solution containing 45% (w:v) sorbitol and 15% (w:v) glycine. Afterwards neither a loss of activity nor an increase in the aggregate content was observed.

A process for the pasteurization of human plasma with the addition of sugar alcohols, amino acids or saccharides is described in EPatent-A-0 139 975. In the pasteurization of plasma the immunoglobulin is protected by the other plasma proteins. The stabilizing effect of albumin on IgG is known.

The present invention relates to a process for the preparation of a pasteurized immunoglobulin preparation, which comprises heating a solution of an immunoglobulin in the presence of a carboxylic acid or one of its salts and/or of a saccharide until pathogens in particular hepatitis viruses or HTLV III ("Aids") viruses, are inactivated (i.e. rendered incapable of reproduction or of being intracellularly or otherwise reproduced).

Conditions suitable for such inactivation are known to the expert. It is customary to heat at about 60° C. for about 10 hours.

This carboxylic acid is preferably an aliphatic carboxylic acid which can preferably be substituted with one or more additional carboxyl groups or one or more amino groups or one or more hydroxyl groups. It preferably contains two to ten carbon atoms. This carboxylic acid is preferably glycine, glutamic acid, citric acid or tartaric acid.

A preferred salt of a carboxylic acid is a soluble metal salt, in particular an alkali metal or alkaline earth metal salt, especially the sodium or magnesium salt.

The salt of glutamic acid which is used is preferably an alkali metal salt, especially the monosodium salt (sodium glutamate).

The carboxylic acids or their salts can be added in an amount up to or exceeding the saturation limit, preferably from 0.4 to 0.6 g per milliliter of the immunoglobulin solution which is to be stabilized.

The saccharide which is preferably used is a mono- or disaccharide, with particular preference for sucrose.

These saccharides are preferably added in an amount of 0.5 to 1.0 g per milliliter of the immunoglobulin solution which is to be stabilized.

The carboxylic acids or their salts or the saccharides can be added in an amount up to or exceeding the saturation limit of the immunoglobulin solution which is to be stabilized.

The addition of these substances may cause a precipitation of the immunoglobulins. In this case, the resulting suspension is nevertheless heated without detrimental effect on the immunoglobulin.

The pH-value is adjusted to 5-8.5, preferably 6.5-7.5, for the heating process.

Using the claimed process it is possible to obtain pasteurized immunoglobulin solutions whose polymer content is below 10%. In the preferred embodiments the polymer content remains unchanged, within the range of experimental error variation of the method, compared with that of the unheated immunoglobulin solution.

The starting material for the process according to the present invention can be a purified immunoglobulin which, in the literature is called gamma-globulin, IgG, immunoglobulin G or fraction II based on J. Am. Chem. Soc. 71, 541 (1949). Immunoglobulins of this type are mainly derived from the step-wise precipitation which result from the fractionation of plasma. Immunoglobulin-containing precipitates are the fraction A of Vox. Sang. 7, 414 (1962), or fraction II and III of J. Am. Chem. Soc. 68, 459 (1946).

It is also possible to use modified immunogloblins as starting materials. Immunoglobulins of this type can be modified by chemical modification, for example sulfitolysis, or enzymatic treatment, for example peptic elimination of the Fc portion. Proteolytic cleavage of the immunoglobulin molecule with pepsin at pH 4 results mainly in $F(ab)_2$ fragments with a molecular weight of about 100,000 and a sedimentation coefficient determined in the analytical ultracentrifuge of about 5 S (S=Svedberg unit).

Products of this type contain uncleaved immunoglobulin of 7 S (molecular weight about 150,000) but virtually no immunoglobulin polymers. However, more extensively fragmented portions with a molecular weight below 5 S are observed at concentrations below 10%.

It has been surprisingly found, that the claimed process is also suitable for solutions of immunoglobulins which contain ethanol.

When purified immunoglobulins are obtained using ethanol, often the final concentration step of the production process consists of a complete precipitation of the immunoglobulins with ethanol and the subsequent removal of the precipitate by centrifugation.

(1962), 7, 414). Fractions of this type contain not only gamma-globulins but also lipoproteins, euglobulins, alpha- and beta-globulins and minor amounts of albumin. The gamma-globulin content is about 40-80 g in 100 g total protein. When 100 g of fraction II+III are dissolved in 250 ml of distilled water, the alcohol content of the solution is 4-5 ml/100 ml. A fraction II+III of this type can therefore be pasteurized in the manner according to the invention.

Table 1 shows the contents of polymeric immunglobulin after application of the process described, compared with the state of the art. In each case, heating at 60° C. was continued for 10 hours. The immunglobulin content was 10-11 g of protein per 100 ml of solution. The pH was 7.

TABLE 1

| Contents in 100 ml of the globulin solution | | | Added to 100 ml of globulin solution | | | | Polymer content before/after heating* (g/100 g globulin) |
|---|---|---|---|---|---|---|---|
| Ethanol (ml) | NaCl (g) | Glycine (g) | Substance | Amount (g) | Substance | Amount (g) | |
| 0 | 0.3 | 2.25 | Ammonium sulfate | 80 | — | — | 1.7   10.8 |
| 4 | 0.1 | 0 | Lysine, HCl | 100 | Glycine | 15 | 3.3   5.5 |
| 0 | 0.3 | 2.25 | Monodosium citrate | 60 | — | — | 1.3   3.4 |
| 4 | 0.3 | 2.25 | " | 60 | — | — | 1.1   27.7 |
| 0 | 0.3 | 2.25 | Mono-Na L-glutamate | 60 | — | — | 1.1   1.4 |
| 4 | 0.3 | 2.25 | " | 60 | — | — | 1.1   4.5 |
| 2 | 0.3 | 2.25 | " | 60 | — | — | 1.2   1.8 |
| 2 | 0.12 | 0 | Glucose | 60 | — | — | 2.3   5 |
| 4 | 0.12 | 0 | " | 100 | Glycine | 15 | 3.0   3.1 |
| 2 | 0.12 | 0 | Fructose | 60 | — | — | 2.3   4.5 |
| 2 | 0.12 | 0 | Galactose | 60 | — | — | 2.3   5.1 |
| 4 | 0.1 | 0 | Sucrose | 100 | Glycine | 15 | 2.2   1.7 |
| 4 | 0.1 | 2.25 | " | 100 | Lysine, HCl | 15 | 3.3   4.1 |
| 4 | 0.1 | 0 | Mono-Na L-glutamate | 60 | Sucrose | 50 | 3.0   4.3 |
| 0 | 0.3 | 2.25 | Sodium tartrate | 50 | — | — | 1.3   3.6 |
| 4 | 0.3 | 2.25 | " | 50 | — | — | 1.1   17.3 |

*Analytical gel chromatography using Ultrogel ACA 34. The transmission signals measured in a continuous flow photometer are converted into extinctions, and an area elution profile is constructed and evaluated.

Dissolution of the precipitate to an approximate 10% solution results in a residual alcohol content which amounts to about 4% by volume. The ethanol is usually removed by freeze-drying or ultrafiltration. If the heating were to be carried out in the alcohol-free solution, for example after ultrafiltration, in the presence of stabilizers it would be necessary to repeat the ultrafiltration to remove these additives subsequently. Thus, to expedite and economize the processing it is advantageous to perform the heating in the presence of ethanol.

It was surprisingly found, that, upon addition of carboxylic acid, no increase in aggregation was observed when the immunoglobulins were heated in the presence of ethanol at 60° C. for prolonged periods, for example 40 h.

It is known that ethanol normally denatures immunoglobulins at elevated temperatures. Accordingly, heating of immunoglobulins even in the presence of carboxylic acids or their salts as stabilizers did produce a higher content of polymers in the presence of alcohol, than in a procedure without alcohol.

An example of an ethanol-containing immunoglobulin solution is a fraction containing gamma-globulin called fraction II+III by Cohn et al., J. Am. Chem. Soc. (1946), 68, pages 459 et seq., or fraction A by Nitschmann (Kistner and Nitschmann, Vox Sang.

The table shows that, after application of the claimed process, the undesired increase in polymers of immunoglobulin is, as a rule, very low even in the presence of alcohol. This finding is, moreover, confirmed by other test methods, for example by determination of the anticomplementary activity.

The contents of the higher molecular weight portions resulting from the heating can be further reduced by known processes.

To this end it is advantageous to replace the added stabilizer, for example by ultrafiltration, by an ionic medium which is suitable for the chosen purification process.

The duration of heating can be varied within certain limits.

To test the efficacy of the process which has been described, an immunoglobulin in solution containing 9.9 g of protein per 100 ml and 3.6 g of ethanol per 100 ml was mixed with 1 g of sucrose and 0.15 g of glycine per 1 ml of solution. Rous sarcoma virus (RSV) was added in a concentration of $1 \times 10^4$ infectious RSV units/ml (U/ml) and then the solution was heated at 60° C. After heating for one hour, the virus content had decreased below the detection limit.

It is evident from Table 2 that the heating which has been described had no effect on the antibody activity.

TABLE 2

| Stabilizer | Amount added (g per 1 ml) | Ethanol ml/100 ml | Heating at 60° C. hours | Antibody titer | | |
|---|---|---|---|---|---|---|
| | | | | Anti-tetanus[1] | Anti-HBsAg[2] | Anti-rubella[3] |
| — | — | — | — | 4048 | 0.22 | 30720 |

TABLE 2-continued

| Stabilizer | Amount added (g per 1 ml) | Ethanol ml/100 ml | Heating at 60° C. hours | Antibody titer | | |
|---|---|---|---|---|---|---|
| | | | | Anti-tetanus[1] | Anti-HBsAg[2] | Anti-rubella[3] |
| Na glutamate | 0.6 | 2 | 10 | 4048 | 0.20 | 30720 |
| Glucose | 0.6 | 2 | 10 | 4048 | 0.19 | 30720 |
| — | — | — | — | 8096 | 0.31 | 30720 |
| Na glutamate | 0.6 | 4 | 10 | 8096 | 0.22 | 30720 |
| Na glutamate/glycine | 0.6/0.15 | 4 | 10 | 8096 | 0.29 | 30720 |
| Na glutamate/sucrose | 0.6/0.5 | 4 | 10 | 8096 | 0.28 | 30720 |
| Sucrose/glycine | 1/0.15 | 4 | 10 | 8096 | 0.27 | 30720 |
| Glucose/glycine | 1/0.15 | 4 | 10 | 8096 | 0.21 | 30720 |

[1]Indirect hemagglutination assay I.H.A. (reciprocal titer)
[2]Radioimmunoassay (in international units/ml)
[3]Elisa (enzyme-linked immunosorbent assay; reciprocal titer)

The examples which follow illustrate the invention:

Example 1

Heating of an immunoglobulin in solution with sodium glutamate 200 ml of a virtually pure solution of immunoglobulin with a protein concentration of 90 g/l were stirred while 120 g of sodium glutamate (monosodium salt of glutamic acid) were adeed. This resulted in the precipitation of the immunoglobulin. The pH-value of the suspension was adjusted to 7; it was then heated and stirred at 60° C. for 10 hours. The mixture was cooled to room temperature and then the precipitate was removed by filtration or centrifugation. The precipitate was dissolved in distilled water. The glutamate was removed by dialysis or ultrafiltration. The solution was adjusted to the desired protein content and made isotonic.

Herefrom 110 ml with a protein concentration of 155 g/l were obtained. The polymer content was 1.6% (1.2% unheated).

Example 2

Heating of an immunoglobulin solution with sucrose and glycine 89 kg of sucrose and 13.3 kg of glycine were added to 89 l of immunoglobulin solution which had a sodium chloride concentration of 1 g/l, a protein concentration of 97 g/l and 3.6% ethanol by volume. The pH-value was adjusted to 7 and then the mixture was heated and stirred at 60° C. for 10 hours. The solution was diluted with 100 l of 0.3 g/100 ml sodium chloride solution and was sterilized by filtration. The stabilizers were removed by ultrafiltration in a known manner. The solution was then made isotonic and adjusted to a protein concentration of 160 g/l.

Consequently 51 l of solution with a polymer content of 2.6% (2% in the unheated solution) were obtained. The residual sucrose concentration was 0.04 g/l.

Example 3

100 g of sucrose and 15 g of glycine were added to 100 ml of sulfonated immunoglobulin with a protein concentration of 100 g/l and a sodium chloride concentration of 3 g/l. The pH-value was adjusted to 7.3 and then the mixture was heated and stirred at 60° C. for 10 hours.

The solution was then cooled to room temperature and diluted with 170 ml of 0.3 g/100 ml sodium chloride solution. The stabilizers were removed by ultrafiltration. The solvent was replaced by a 0.3 g/100 ml sodium chloride solution. The solution of the immunoglobulin was made isotonic and adjusted to a protein concentration of 50 g/l.

195 ml of solution with a polymer content of 5.6% (5.8% in the unheated solution) were obtained by this procedure.

Example 4

13.7 l of an immunoglobulin solution which had undergone peptic cleavage (with a protein concentration of 180 g/l and a sodium chloride concentration of 3.2 g/l) were diluted with 13.5 l of a 0.3 g/100 ml sodium chloride solution. Then 27.2 kg of sucrose and 4.08 kg of glycine were added. At pH 7 the mixture was then heated to 60° C. and stirred for 10 hours. The solution was then cooled to room temperature and diluted with 45 l of 0.3 g/100 ml sodium chloride solution. Sterilization by filtration was followed by substantial removal of the added stabilizers by ultrafiltration. The solution was then made isotonic and adjusted to a protein concentration of 50 g/l. 48 l of solution with a residual sucrose concentration of 0.01 g/l were obtained. The content of components of defined molecular weights was determined in an analytical ultracentrifuge as follows:

| Starting material: | S less than 5 = 8.8% |
| --- | --- |
| | S about 5 = 75.5% |
| | S about 7 = 15.7% |
| | S greater than 7 = 0% |
| Heating final product: | S less than 5 = 8.1% |
| | S about 5 = 77.5% |
| | S about 7 = 14.4% |
| | S greater than 7 = 0% |

Example 5

Heating of a dissolved ethanol-containing fraction II+III in the presence of ethanol 200 g of fraction II+III were dissolved under stirring in 500 ml of distilled water. To the solution (about 700 ml) 700 g of sucrose and 0.3 to 0.2 mol/l glycine were added. The pH-value was adjusted to about 7 and the solution was then heated and stirred at 60° C. for 10 hours. The heated solution was then fractionated. 304 ml of immunoglobulin solution with a protein concentration of 66 g/l were obtained. The polymer content was 1.1%.

For comparison an unheated treatment also using 200 g of fraction II+III produced 208 ml of immunoglobulin solution with a protein concentration of 96.8 g/l. The polymer content was 2.0%.

We claim:

1. A process for the preparation of a pasteurized immunoglobulin preparation, which comprises heating a solution of an immunoglobulin containing ethanol, where said ethanol is present in amounts ranging from at least some ethanol to less than about 5 percent by volume, in the presence of at least one of the group consisting of a carboxylic acid or one of its salts and a saccharide until viable pathogens are inactivated.

2. The process as claimed in claim 1, wherein the carboxylic acid is an optionally substituted aliphatic carboxylic acid.

3. The process as claimed in claim 2, wherein the carboxylic acid is an aliphatic carboxylic acid which has two to ten carbon atoms and is substituted with one or two additional carboxyl groups, one or two amino groups and/or one or more hydroxyl groups.

4. The process as claimed in claim 3, wherein the carboxylic acid is selected from a member of the group consisting of glycine, glutamic acid, citric acid and tartaric acid.

5. The process as claimed in claim 1, wherein the saccharide is selected from a member of the group consisting of a mono- and disaccharide.

6. The process as claimed in claim 1 wherein the saccharide is selected from a member of the group consisting of glucose, fructose, galactose and sucrose.

7. The process as claimed in claim 1 wherein said viable pathogens that are inactivated are hepatitis viruses or HTLV III ("Aids") viruses.

8. The process as claimed in claim 1 wherein said ethanol is present in an amount ranging from 2 to 5 percent, by volume.

9. A process for the preparation of a pasteurized immunoglobulin preparation, which comprises heating a solution of an immunoglobulin containing ethanol, where said ethanol is present in amounts ranging from at least some ethanol to less than 5 percent by volume, in the presence of a carboxylic acid or one of its salts and of a saccharide until viable pathogens are inactivated.

10. The process according to claim 9 where said carboxylic acid is an amino acid.

11. The process according to claim 9 where said saccharide is saccharose.

* * * * *